May 5, 1953 F. J. KEPLINGER Plant Pat. 1,183
STRAWBERRY PLANT
Filed Dec 26, 1950
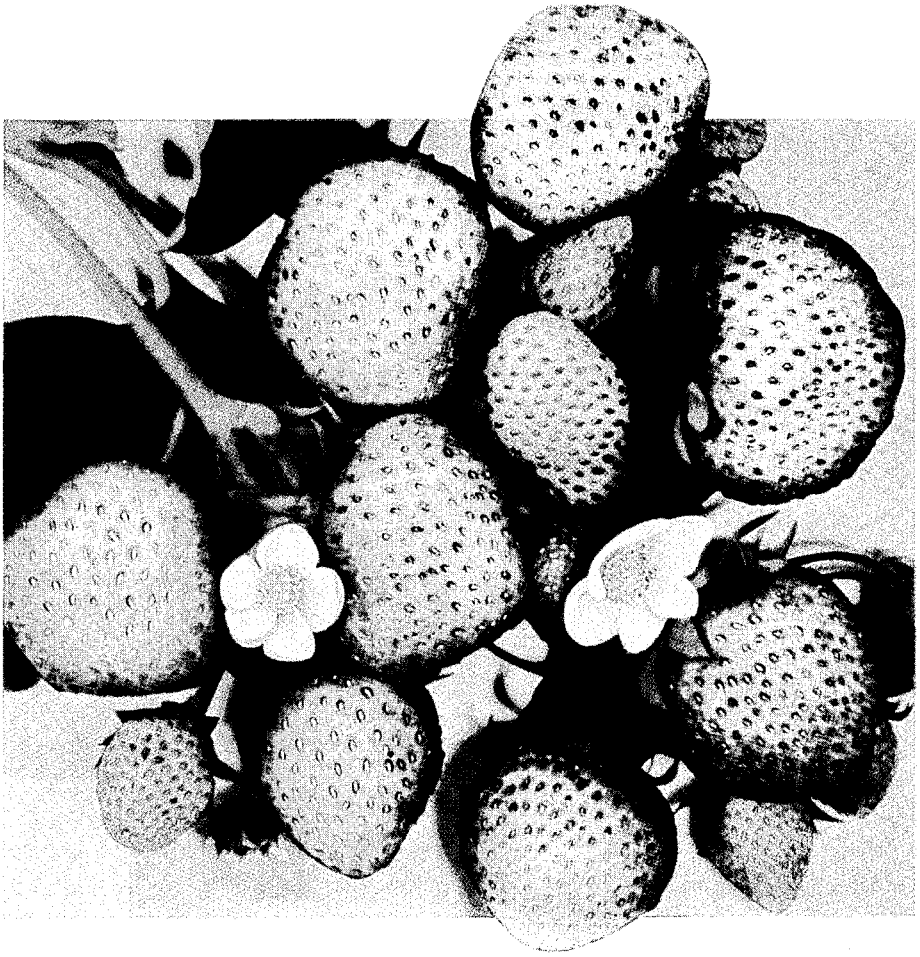
INVENTOR
Frank J. Keplinger
By Robb & Robb,
Attorneys Patented May 5, 1953

Plant Pat. 1,183

UNITED STATES PATENT OFFICE 1,183

STRAWBERRY PLANT

Frank J. Keplinger, Farwell, Mich., assignor to Emlong Nurseries, Inc., Stevensville, and Carl A. Stahelin, Bridgman, Mich., jointly Application December 26, 1950, Serial No. 202,622

1 Claim. (Cl. 47—62)

My present invention relates to a new and distinct variety of strawberry plant, which originated as a seedling resulting from seed of the variety "Gem" pollenized with pollen of the same unpatented variety.

The object of my invention has been to produce a new variety of strawberry plant of the everbearing type, having greater fruit productivity and capable of greater continuity of fruit production throughout the period from spring until fall than is the case with other standard everbearing varieties.

A further object of my invention has been to produce such a new variety of strawberry plant having the fruit production characteristics mentioned and capable of producing high quality fruit under adverse conditions, especially those conditions involving poor soil and partial drought.

For the accomplishment of the foregoing special purposes, I have conducted a careful program of hybridization as well as inbreeding and selection, with a view to producing new varieties of strawberry plants having the characteristics above referred to.

The results of the specific inbreeding program have been to produce my present new and distinct variety of strawberry plant, characterized by its greater fruit productivity and higher fruit production continuity from spring until frost; its higher plant multiplication capacity; the larger size and high quality and brilliant red color of its fruit; its ability to thrive under adverse weather and soil conditions; the short spacing of plants on and the red color of its runner stems; its dark green, glossy foliage; and its sturdy fruit stems.

While my new variety more closely resembles its parent "Gem," it differs from the latter variety as it does from all other varieties in the characteristics above mentioned. Additionally, it may be noted that the leaves of my new variety do not have the bluish cast characteristic of "Gem" leaves, the foliage of my new variety being distinctive in reference to its dark green, glossy foliage. Also it may be noted that, in contrast to the variety "Gem" in which the individual plants are spaced extraordinarily far apart on the runner stems, my new variety is distinguished by the close spacing of the plants on the runner stems. The color of the leaves and the spacing of plants on the runner stems of my new variety are distinctive characteristics as compared with plants of the "Gem" variety grown at Farwell, Michigan, under exactly the same conditions. In this connection it may be noted that my new variety is superior to other varieties in reference to its capacity for plant multiplication. My new variety, for example, is capable of producing two to three times as many plants per acre as the well-known unpatented variety "Streamliner."

My new variety is much more upright growing than "Gem." The flesh of the fruit of my new variety is red throughout whereas the berries of "Gem" variety are inclined to be white. The shape of the berry of my new variety is more round whereas the berries of "Gem" variety are quite pointed. The foliage of my new variety differs from the foliage of "Gem" variety, the foliage of my new variety having a bluish cast, whereas the foliage of "Gem" variety has a green cast. The flavor of the berries of my new variety is rich and distinctive as compared with the flavor of berries of all other strawberry varieties with which I am familiar.

In reference to its high productivity characteristic, my new variety has been tested at the Ohio Agricultural Experiment Station along with seven other well-known everbearing varieties, viz., Gemzata, Mastodon, Streamliner, Brunes Marvel, Wayzata, Gem, Superfection (all unpatented varieties), the test being conducted under similar conditions in the vicinity of Columbus, Ohio. These tests showed that the productivity of the other seven varieties ranged from about 500 quarts of berries per acre to something under 5500 quarts per acre for the most productive of these other varieties. In these tests my new variety produced fruit at the rate of 7000 quarts per acre per year, which was over 1500 quarts per acre more than the production of "Superfection," the largest producer of the other varieties so tested.

My new variety has been found to be capable of producing a heavy crop of fall berries above average size, under relatively poor weather and soil conditions. My new variety has also been found capable of producing a high quality spring crop of berries not exceeded by the best single crop of June varieties, a characteristic that is not found in any other everbearing variety. My new variety furthermore is capable of producing fruit continuously from June throughout the summer until frost, whereas other varieties considered as everbearing produce abundantly in the spring, sparsely during the summer, and abundantly again in the fall.

My new variety has proved superior to all of the other varieties tested, as above mentioned, in reference to the ability to produce berries under adverse conditions, especially conditions involving poor soil and partial drought. My new variety is also characterized by its exceedingly long plant life span.

The fruit of my new variety is identifiable by its brilliant blood red color. Its red color extends clear through the meat of the berry. The berries of my new variety are relatively large, averaging one and one-half inches in length and three-quarters of an inch in breadth, and they are of irregular wedge-shape. The berries are also characterized by their relatively small cores.

The berries of my new variety possess a unique strawberry flavor which may be best described as rich with a brisk yet mellow tang. The berries of my new variety are superior to those of other varieties for freezing packaging, because the berries of my new variety do not lose their flavor when thawed; the berries may be preserved with equal facility by freezing either in home freezers or commercial freezers, and this is an especially desirable characteristic.

The plants of my new variety are distinctive in reference to the dark green, glossy foliage and sturdy fruit stems.

My new variety has been found to retain its distinctive characteristics through successive asexual reproduction.

My new variety has been asexually reproduced by runners or stolens at Farwell, Michigan.

The accompanying drawing, forming a part hereof, shows a typical plant of my variety, illustrating the berries, both green and ripe.

The following is a detail description of my new variety:

Plant: Growth—vigorous; root—vigorous; crown—simple, medium.

*Leaves.*—Many—medium; petiole length—medium, stout; color—dark green with red on exposure; pubescence—abundant, spreading. Serrations—irregular, green tinged. Leaflet surface—glossy; color lower surface—dark green; color upper surface—dark green. Pubescence—abundant.

*Runners.*—Appear during fruiting; numerous; medium.

*Flower stems.*—Medium.

*Bloom.*—Medium; date full bloom—June; flowers—many; breadth primary, ½″; secondary, ⅞″; perfect. Filaments of stamens—long; pollen—abundant.

*Fruiting stems.*—Medium; decumbent; branches of truss—many.

*Culture.*—thorough.

*Frost resistance.*—Good.

*Drought resistance.*—Good.

Fruit: Condition when described—prime.

*Size.*—Large, constant throughout. Average fruit length, 1½″; breadth 1⅜″.

*Form.*—Uniform; regular; conical; pointed.

*Stems.*—Radical—short.

*Calyx.*—Green after picking; even with surface; tenacious. Upper surface color—light; pubescence—abundant. Lower surface—light green; pubescence—abundant.

*Surface.*—Glossy; seeds—inconspicuous.

*Core.*—Solid. Color—red.

*Flesh.*—Juicy. Texture—firm.

*Flavor.*—Rich.

*Quality.*—Best. Shipping quality—good.

*Color of berries when fully ripe.*—Blood Red, plate 820/3, page 166 of British Horticultural Color Guide.

The primary characteristics referred to have been found to be fixed in the asexual reproduction of the plant.

I claim:

A new and distinct variety of strawberry plant substantially as herein disclosed, characterized by the brilliant red color and larger size of its fruit; its greater fruit productivity and higher fruit production continuity from spring until frost; its higher plant multiplication capacity; its ability to thrive under adverse weather and soil conditions; the short spacing of plants on and the red color of its runner stems; and its dark green, glossy foliage.

FRANK J. KEPLINGER.

No references cited.